United States Patent [19]
Urashima et al.

[11] Patent Number: 6,060,486
[45] Date of Patent: May 9, 2000

[54] CARBOSTYRIL DERIVATIVE FOR CURING OPHTHALMOLOGICAL DISEASES

[75] Inventors: Hiroki Urashima; Yasuhiro Takeji, both of Ako; Hisashi Shinohara, Gifu; Shigeki Fujisawa, Takasago, all of Japan

[73] Assignee: Otsuka Pharmaceutical Co., Ltd., Tokyo, Japan

[21] Appl. No.: 09/051,194

[22] PCT Filed: Oct. 1, 1996

[86] PCT No.: PCT/JP96/02850

§ 371 Date: Jun. 12, 1998

§ 102(e) Date: Jun. 12, 1998

[87] PCT Pub. No.: WO97/13515

PCT Pub. Date: Apr. 17, 1997

[30] Foreign Application Priority Data

Oct. 12, 1995 [JP] Japan .................................. 7-263896
Mar. 14, 1996 [JP] Japan .................................. 8-057337

[51] Int. Cl.$^7$ .................................................. A61K 31/445
[52] U.S. Cl. ............................................ 514/319; 514/912
[58] Field of Search ...................................... 514/319, 912

[56] References Cited

FOREIGN PATENT DOCUMENTS

| | | |
|---|---|---|
| 0 543 018 | 5/1993 | European Pat. Off. . |
| 2 123 825 | 2/1984 | United Kingdom . |
| WO 93/23043 | 11/1993 | WIPO . |
| WO 94/21612 | 9/1994 | WIPO . |
| WO 95/11026 | 4/1995 | WIPO . |
| WO 96/04911 | 2/1996 | WIPO . |

*Primary Examiner*—Zohreh Fay
*Attorney, Agent, or Firm*—Finnegan, Henderson, Farabow, Garrett & Dunner, L.L.P.

[57] ABSTRACT

The present invention provides an agent for curing ophthalmological diseases which contains, as the active ingredient, a carbostyril derivative or salt thereof represented by the general formula (I), (I)

[structure: carbostyril with $CH_2CH$—$COOH$ / $NHCO$ — phenyl—R]

(wherein R is a halogen atom) particularly, the invention provides effective agent for curing xerophalmia (dry eye) syndrome.

16 Claims, 5 Drawing Sheets

CARBOSTYRIL DERIVATIVE FOR CURING OPHTHALMOLOGICAL DISEASES

FIELD OF THE INVENTION

The present invention relates to an agent for curing ophthalmological diseases which contains, as the effective ingredient, a carbostyril derivative or salt thereof. More particularly, the present invention relates to an agent for curing ophthalmological diseases, especially xerophthalmia syndrome, commonly called as "dry eye" which contains, as the effective ingredient, a carbostyril derivative or salt thereof represented by the general formula (I),

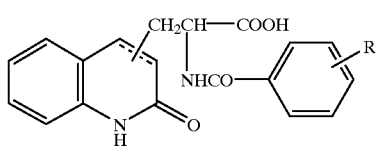

(wherein R is a halogen atom, the substituted position of the side-chain of the formula,

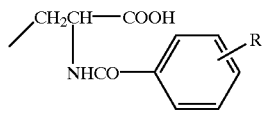

is 3- or 4-position in the carbostyril skeleton, and the carbon-carbon bond between 3- and 4-positions in the carbostyril skeleton is a single bond or a double bond), more preferably 2-(4-chlorobenzoylamino)-3-(2-quinolon-4-yl) propionic acid or salt thereof.

BACKGROUND ART

The carbostyril derivatives represented by the general formula (I) and process for producing the same are described in Japanese Patent Publication No. 10 63-35623, the usefulness of carbostyril derivatives as anti-gastric ulcer agents is described in Japanese Patent Application Kokai (Laid-open) No. 3-74329, and processes for producing those carbostyril derivatives having optical activities are described in Japanese Patent Application Kokai (Laid-open) No. 3-145468.

Further, the inhibitory effect of carbostyril derivatives of the present invention on reactive oxygen metabolites is described in Japan. J. Pharmacol., Vol. 49, pp. 441–448 (1969), and the protectability of gastric mucous membrane by carbostyril derivatives of the present invention is described in Folia Pharmacol. Japon., Vol. 97, pp. 371–380 (1991).

Furthermore, the usefulness of carbostyril derivatives as agents for curing diabetes mellitus is described in International Publication No. WO 92/21342, the usefulness of carbostyril derivatives as agents for protecting the intestinal mucosa from disorders is described in International Publication No. WO 94/12182, and the usefulness of carbostyril derivatives as agents for inhibiting the reduction in secretion of somato-statin is described in International Publication No. WO 93/24043.

"Dry eye" symptom (xerophthalmia) is a pathogenic state (pathema) of the eye in which the surface of the eye cannot be maintained to normal condition due to a shortage of the amount of tears. Furthermore, the mucous membranes (the epithelia of the cornea and conjuctiva) on the surface of the eye may be caused not only by an abnormal shortage of the amount of tears, but also by an abnormal nature of tears [Cf. DORAI-AI (dry eye), page 11, by Kazuo TSUBOTA, published from NIPPON-HYORONSHA]. In addition to the above, such dry eye symptoms may be observed in case of Sjögren's syndrome with abnormal states (the amount and nature) of tears. Also, there have been known that the dry eye symptom may be occurred in the end-stage of Stevens-Johnson syndrome and observed that the cornea and conjuctiva are injured.

Tear fluid (lacrima) is a very thin liquid layer having 7 $\mu$m in thickness, which covers the outmost (extima) layer of the front of eye, and having trilaminar structure consisting of lipid layer, aqueous layer and mucoid layer. The lipid layer being existed on the outmost surface layer of the tear fluid is an oily film, which is produced and secreted mainly from the meibomian glands located in periphery of the eyelids, and covers all over the aqueous layer. The lipid layer is considered to have the function for preventing evaporation of water from the aqueous layer. The aqueous layer is a portion of so-called "tears" which occupies the most thickness of the tear fluid layer, and 98% of the constituent thereof is water. A pathogenic state in decreasing of the amount of this aqueous layer is so-called as "dry eye" symptom. The mucoid layer covers the hydrophobic surface of the epithelium of the cornea, this mucoid layer changes the hydrophobic surface of the epithelium of the cornea to hydrophilic nature to maintains and extends the aqueous layer in the tear fluid, so that the aqueous layer can be able to maintain on the surface of the epithelium of the cornea. Cells related to producing said mucoid layer are goblet cells being contained in the conjuctiva.

As explained above, the tear fluid which may cause directly to introduce the "dry eye" symptom is involved in various tissue cells. Also the concept of "dry eye" symptom is complicated, so that a common type of eye drop preparation can only gives a temporary medical measure, thus at the present stage fundamental method for medical treatment of the "dry eye" symptom have not been found yet. So that new method and new agent for curing the "dry eye" symptom have been eagerly expected.

DISCLOSURE OF THE INVENTION

Figure 1:
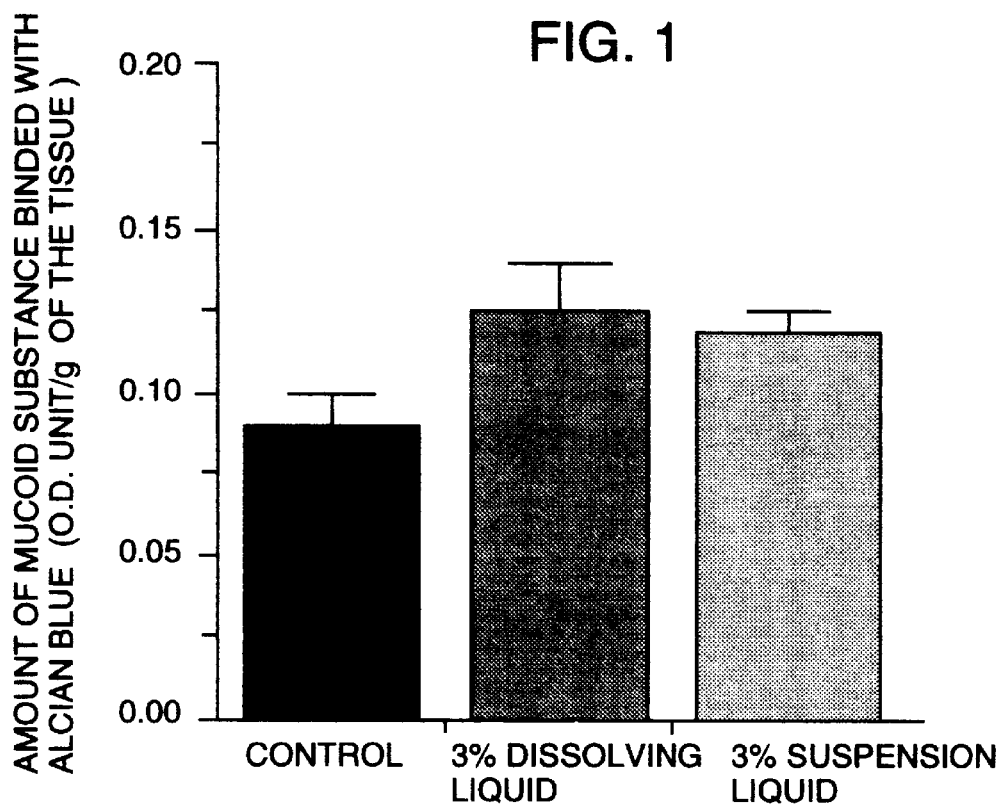
FIG. 1 shows a figure relating to the effect of carbostyril derivative of the present invention against the amount of mucoid substance covering the conjuctiva in normal rabbits determined by Alcian blue binding method.

As the results of extensive research work, the present inventors have found the facts that carbostyril derivatives represented by the general formula (I), particularly among of these, 2-(4-chlorobenzoylamino)-3-(2-quinolon-4-yl) propionic acid or a salt thereof possess the effect for increasing the number of the goblet cells, the effect for increasing secretion of mucus of the front of the eye, the effect for accelerating proliferation of the corneal epithelium cells, as well as the effect for increasing secretion of tear fluid, thus said carbostyril derivative is useful as an agent for curing xerophthalmia syndrome, and finally the present invention has been completed.

Carbostyril derivatives represented by the general formula (I), particularly among of these, 2-(4-chlorobenzoylamino)-3-(2-quinolon-4-yl)propionic acid or a salt thereof increases the production of ophthalmological mucin by increasing the number of goblet cells, as the results said compound prevents decreasing the amount of mucin in case of the "dry eye" syndrome, while said compound of the present invention increases the amount of mucus of the eye as to maintain the aqueous layer in the tear fluid. Further, said compound of the present invention shows the effect for increasing the amount of tear fluid, thus said compound of the present invention is useful as an agent for curing the "dry eye" syndrome. Additionally, said compound of the present invention is an agent useful not only for curing Sjögren's syndrome and Stevens-Johnson syndrome, which shows the dry eye symptom, but also useful as an agent for preventing and/or curing the second disease (deuteropathy) caused by the "dry eye" symptoms or various ophthalmological diseases which are resulted from decreasing the number of goblet cells and lowering the amount of mucus. In case of the "dry eye" symptom, the eye is very sensitive to be injured, because the surface of the eyeball is dried. In this connection, the compound of the present invention is useful as the active ingredient to be contained in an agent for curing the wound of the surface of the eye, particularly an agent for curing wound of the corneal epithelium or an agent for intraocular perfusion and agent for washing used in ophthalmological operations (including operations of cataract, the vitreous body and glaucoma), because the compound has the effect for accelerating the proliferation of the corneal epithelium cells.

An agent for curing ophthalmological diseases of the present invention can be prepared into various forms of common pharmaceutical preparations by formulating the carbostyril derivative represented by the general formula (I) or salt thereof as the effective ingredient. Such forms of pharmaceutical preparations are prepared by formulating the carbostyril derivative (I) with diluents or excipients, for example, fillers, extenders, binders, wetting agents, disintegrants, surfactants, lublicants and the like which are commonly employed.

The pharmaceutical preparations can be shaped into various forms depending upon the curing purposes, thus typical examples of the forms are ophthalmologically acceptable pharmaceutical preparations, such as eye drop preparations and oculentums and the like.

In addition to the eye drop preparations and oculentums, the pharmaceutical preparations can be shaped into tablets, pills, powders, liquid medicines, suspensions, emulsions, granules, capsules, suppositories, injection preparations (liquids, suspensions and the like), aerosol preparations, syrup preparations, preparations for external use and the like. Further, sustained release preparations can also be prepared by formulating with suitable resins.

In case of formulating the pharmaceutical preparations into eye drops, oculentums and the like, they are prepared in accordance with common method by using usual vehicles (diluting agents) acceptable to pharmaceutical preparations for ophthalmological use. Thus, they are prepared by mixing the effective ingredient with a suitable diluting agent, then the mixture is subjected to sterilizing treatment.

For example, in case of preparing oculentums, various base materials which are widely used in this field, such as emulsion type ointment base, water-soluble type ointment base, suspension type ointment base and the like can be employed. As to typical examples of these base materials, white petrolatum, refined lanolin, liquid paraffin and the like can be exemplified. In case of producing eye drop preparations, sterilized distilled water can be employed as typical diluting agent.

If necessary, a dissolving additive, a buffering agent, an antioxidant, a preservative, an isotonic agent, a pH-controlling agent and the like can be formulated with an pharmaceutical preparation applicable for ophthalmological purpose. As to the dissolving additives, carboxymethyl cellulose-Na; polyoxyethylene glycol ethers, such as polyoxyethylene lauryl ether, polyoxyehylene oleyl ether and the like; polyethylene glycol higher fatty acid esters, such as polyethylene glycol monolaurate, poyethylene glycol monooleate and the like; polyoxyethylene sorbitan monolaurate; polyoxyethylene fatty acid esters and the like can be exemplified. As to the buffering agents, sodium phosphates, sodium hydrogen phosphate, potassium hydrogen phosphate, nitric acid, sodium nitrate, citric acid, sodium citrate, tartaric acid, sodium tartarate, acetic acid, sodium acetate, $\epsilon$-aminocaproic acid, sodium glutamate and the like can be exemplified. As to the antioxidants, sodium sulfite, sodium pyro-sulfite, sodium bisulfite, sodium thiosulfite, ascorbic acid and the like can be exemplified. As to the preservatives, chlorobutanol, benzalkonium chloride, benzethonium chloride, phenylmercury salts, thimerosal, phenethyl alcohol, methylparaben, propylparaben and the like can be exemplified. As to the isotonic agents, sodium chloride, glucose, D-mannitol, glycerin and the like can be exemplified. As to the dissolving agents, N-methyglucamine can be employed. As to the pH-controlling agents, sodium hydroxide, hydrochloric acid and the like can be exemplified.

For the purpose of shaping into the form of tablets, any known carriers which are used widely in this field can be applied, for example, excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinyl pyrrolidone and the like; disintegrators such as dry starch, sodium alginate, agar powder, laminarin powder, sodium hydrogen-carbonate, calcium carbonate, polyoxyethylene sorbitan fatty acid esters, sodium lauryl sulfate, monoglycerides of stearic acid, starch, lactose and the like; disintegration inhibitors such as white sugar, stearin, cacao butter, hydrogenated oils and the like; absorption accelerators such as quaternary ammonium base, sodium lauryl sulfate and the like; humectants such as glycerin, starch and the like; adsorbents such as starch, lactose, kaolin, bentonite, colloidal silicic acid and the like; lubricants such as refined talc, stearic acid salts, boric acid powder, poly-ethylene glycols and the like. In case of necessity, the tablets can be prepared in the form of common coated tablets, for example, sugar-coated tablets, gelatin film-coated tablets, enteric film-coated tablets, film-coated tablets, or in the form of double-layers tablets, multiple-layers tablets and the like.

For the purpose of shaping into the form of pills, any known carriers which are widely used in this field can be applied, for example, excipients such as glucose, lactose, starch, cacao butter, hydrogenated vegetable oils, kaolin, talc and the like; binders such as arabic gum powder, tragacanth gum powder, gelatin, ethanol and the like; and disintegrators such as laminarin, agar-agar and the like can be exemplified.

For the purpose of shaping into the form of suppositories, any known carriers which are widely used in this field can be applied, for example, polyethylene glycols, cacao butter, higher alcohols, esters of higher alcohol, gelatin, semi-synthesized glycerides and the like can be exemplified.

For the purpose of shaping into the form of injection preparations, they can be prepared to solutions, emulsions or suspensions. Generally they are sterilized and preferably made isotonic to the blood. In preparing the injection preparations as in the form of solutions, emulsions or suspensions, any known diluents which are widely used in this field can be applied. For example, water, ethanol, propylene glycol, ethoxylated isostearyl alcohol, polyoxy-lated isostearyl alcohol, fatty acid esters of polyoxy-ethylene sorbitan and the like can be exemplified. In the case of make the injection preparations isotonic to the blood, sufficient amount of sodium chloride, glucose or glycerin may be contained therein. Additionally, a dissolving adjuvant, a buffer solution, an analgesic agent and the like which are commonly used may be contained therein. In case of necessity, a coloring agent, a preservatives, a perfume, a flavoring agent, a sweetening agent and other medicines may be contained therein.

External preparations are prepared in the form of common pharmaceutical preparations for external use. As to common pharmaceutical preparations for external use are including, for example, a liquid medicine, a medicinal oil, a lotion, a liniment, an oleoginous ointment, an emulsion type ointment, such as O/W type hydrophilic ointment and W/O type water-absorbing ointment, a water-soluble ointment, a pasta, a plaster, a patch, a cream, an emulsion and the like, and these forms of pharmaceutical preparations for external use are not restricted within the scope of these examples. Each one of these forms of pharmaceutical preparations for external use can be prepared by common methods.

In shaping of these external preparations, various base materials which are widely used in this field can be also applied. For example, at least one oleaginous base can be used singly, or mixture of two or more of them can be used widely; or at least one water-soluble ointment base can be used singly, or mixture of two or more of them can be used widely. Concrete examples of these ointment base are fats and oils such as peanut oil, sesame oil, soybean oil, safflower oil, avogado oil, sunflower oil, corn oil, rapeseed oil, cotton seed oil, castor oil, camellia oil, coconut oil, olive oil, poppy seed oil, cacao butter, beef tallow, lard, wool fat and the like; modified bases obtained by subjecting these fats and oils to chemical changes such as hydrogenation; mineral oils such as petrolatum, paraffin, silicone oil, squalane and the like; higher fatty acid esters such as isopropyl myristate, n-butyl myristate, isopropyl linoleate, acetyl ricinoleate, stearyl ricinoleate, propyl ricinoleate, isopropyl ricinoleate, isobutyl ricinoleate, heptyl ricinoleate, diethyl sebacate and diisopropyl adipate; higher aliphatic alcohols such as cetyl alcohol and stearyl alcohol; waxes such as bleached bees wax, spermaceti, Japan wax, lanolin, carnauba wax, shellac wax and the like; higher fatty acids such as stearic acid, oleic acid, palmitic acid and the like; mixtures of mono-, di- and tri-glycerides of saturated or unsaturated fatty acids having 12 to 18 carbon atoms; polyhydric alcohols such as ethylene glycols, polyethylene glycols, propylene glycol, polypropylene glycols, glycerin, batyl alcohol, pentaerythritol, sorbitol, mannitol and the like; gummy substances such as arabic gum, benzoic gum, guaiacum, tragacanth gum and the like; water-soluble natural high molecular compounds such as gelatin, starch, casein, dextrin, pectin, sodium pectate, sodium alginate, methyl cellulose, ethyl cellulose, carboxymethyl cellulose, hydroxyethyl cellulose, hydroxypropyl cellulose, nitrocellulose, crystalline cellulose and the like; water-soluble synthetic high molecular compounds such as polyvinyl alcohol, poly(vinyl methyl ether), polyvinyl pyrrolidone, sodium polyacrylate, carboxyvinyl polymer, polyethyleneimine and the like; nonionic, anionic, amphoteric and cationic surfactants; ethanol, isopropanol and water, can be exemplified.

To the pharmaceutical preparations for external use, there can be added common additives such as a geling agent, a preservative, an antioxidant, a buffer solution, a pH controlling agent, a wetting agent, an antiseptic agent, a coloring agent, a flavoring agent, a pigment, a thickening agent, a metal chelating agent and the like.

Aerosol type preparations can be prepared generally by formulating a sterilized solution or suspension of the carbostyril derivative of the general formula (I) with a propellant. In case of shaping in the form of a solution or suspension, any one of known diluents which are commonly used in this field can also be used, thus the diluents which are exemplified in formulating the injection preparations can be used. As to the propellant, any one of the propellants which are commonly used in this field can also be used, thus, liquefied gas propellants such as chlorofluorocarbons like dichlorodifluoromethane or trifluorodichloroethane; compressed gas propellants such as nitrogen gas, carbon dioxide gas and the like can be exemplified. The aerosol type preparations may further contain a common solubilizing adjuvant, a buffering agent, and the like, and if necessary, a coloring agent, a preservative, a perfume, a flavoring agent, a sweetening agent may be added thereto.

The amount of the effective ingredient to be contained in the agents for curing ophthalmological diseases of the present invention is not specifically restricted and can be selected from a wide range, and generally the amount may be selected within the range of from 0.005 to 5% by weight, preferably 0.01 to 3% by weight.

Method for administering the agent of the present invention is not specifically restricted. Thus, the agent may be administered by methods similar to those employed in usual pharmaceutical preparations acceptable for ophthalmological use, depending upon the form of preparation, the age of patient, the distinction of sex and other conditions, the degree of disease condition of the patient.

As to a typical method for administration of the agent of the present invention, for example, an oculentum is administered by coating on the eye. An eye drop preparation is administered by a method similar to that of employed in common eye drop preparation, for example, 1 to 2 drops of an eye drop preparation is dropped in the eye from a suitable eye drop container. Further, an eye drop preparation may be administered in the eye by use of a spraying device.

As to other methods for administration of the agent of the present invention, for example, tablets, pills, a liquid preparation, a suspension preparation, an emulsion preparation, a granular preparation, a syrup preparation and a capsule preparation are administered orally. An injection preparation is administered singly or in combination with a common auxiliary solution such as a glucose solution and/or an amino acid solution, intravenously. In case of necessity, the injection preparation is administered singly intramuscularly, intradermally, subcutaneously or intraperitoneally. A suppository is administered intrarectally.

Dosage of the agent of the present invention may be suitably selected depend upon the method for administration, the age of patient, the distinction of sex, and other conditions, as well as the degree of disease condition of the patient and other related factors, and generally an agent acceptable for ophthalmological use, for example an eye drop or an olculentum is administered 1 to 15 times a day, preferably within a range of 1 to 10 times a day.

EXAMPLES

An agent for curing ophthalmological disease of the present invention will be explained specifically by illustrating an example of pharmaceutical preparation and pharmacological experiments.

Example of Pharmaceutical Preparation 1

| | |
|---|---|
| 2-(4-Chlorobenzoylamino)-3-(2-quinolon-4-yl)propionic acid | 0.20 g |
| Benzalkonium chloride | 0.01 g |
| Sodium dihydrogen phosphate | 0.56 g |
| Potassium dihydrogen phosphate | 0.80 g |
| Distilled water | q.s. |
| Total | 100.00 ml |

Each one of the above-mentioned ingredients are dissolved in distilled water, then the resulting solution was sterilized and filtrated by using a suitable filter paper to prepare an agent of the present invention in the form of an eye drop preparation.

Pharmacological Test 1

(1) Test Liquids

As to the specific example of the effective ingredient of the agents for curing ophthalmological diseases of the present invention, 2-(4-chlorobenzoyl-amino)-3-(2-quinolon-4-yl)propionic acid (hereinafter referred to as the compound of the present invention) was used and prepared the following dissolving liquid and suspension liquid, and used them as test liquids.

| a) 3% Dissolving liquid | |
|---|---|
| The compound of the present invention | 3.00 g |
| Meglumine (N-Methylglucamine) | 2.64 g |
| Concentrated glycerin | 1.80 g |
| Hydrochloric acid | q.s. |
| 10% Benzalkonium | 0.10 ml |
| Water (an adequate amount was added to adjust the whole volume to:) | 100 ml |

-continued

| | |
|---|---|
| pH (the pH value was adjusted to within the range of:) | 8.3 to 9.3 |
| b) 3% Suspension liquid | |
| The compound of the present invention | 3.00 g |
| Sodium dihydrogenphosphate | 0.40 g |
| Disodium hydrogenphosphate | 0.47 g |
| Sodium chloride | 0.50 g |
| Carboxymethyl cellulose-Na | 0.20 g |
| Polysorbate 80 | 0.16 g |
| 10% Benzalkonium chloride | 0.10 ml |
| Water (an adequate amount was added to adjust the whole volume to:) | 100 ml |
| pH (the pH value was adjusted to within the range of:) | 6.5 to 7.5 |

On the other hand, physiological saline was used as the control test in place of the test liquids.

(2) Experimental Method and the Results

To both eyes of 3 normal rabbits, the above-mentioned test liquid were administered by eye drop, in an amount of 50 $\mu$l/one eye/one administration. Each of the test group and the control group consists of 3 rabbits, thus, 6 eyes were used in each group. The administration was conducted 4 times a day, and was continued for 2 weeks. After that, each one of the rabbits was killed, then the following 3 items of tests were conducted.

(i) Measurement of the amount of mucoid substance covering on the surface of the conjuctiva (Measurement by Alcian Blue Binding Method)

The above-mentioned normal rabbits were killed, and the whole conjunctivae of the rabbits were enucleated. Next, the enucleated conjunctivae were washed with an ice-cooled aqueous solution of 0.25 M sucrose, and weight of each of the tissue of conjunctivae was measured.

The conjuctiva thus treated was incubated in 10 ml of 0.1% Alcian Blue solution at room temperature for 1.5 hours, then was washed with an aqueous solution of 0.25 M sucrose for 15 minutes, further washed with the same solution for 45 minutes. The conjuctiva thus obtained was further incubated in 10 ml of an aqueous solution of 0.5 M $MgCl_2$ for 2 hours, so as to extract the colorant being binded with mucoid layer of the conjunctiva. The extract thus obtained was washed with 10 ml of diethyl ether, and the optical density of the aqueous layer was measured at 605 nm, and the optical density per weight of the tissue (O.D. unit/g of tissue) was calculated (mean value±S.E., n=4 eyes). The results are shown in FIG. 1.

As can be seen from FIG. 1, the amount of the colorant (Alcian blue) being binded with the mucoid substance covering on the conjuctiva of the normal rabbits of the test group, to which 3% dissolving liquid and 3% suspension liquid (both of them containing the compound of the present invention, respectively) were administered by eye drop, were measured in the larger value as compared with that measured in the rabbits of the control group. Thus, the compound of the present invention shows the effect for increasing the amount of the mucoid substance covering the surface on the conjuctiva.

(ii) Measurement of the number of the goblet cells contained in the conjuctiva (Measurement by Method of Impression Cytology)

The portion of the bulbar conjuctiva, which is located closely to the nasolactimal duct at the upper position of the eye of the rabbit being treated with the above-mentioned test liquids, was slightly dried, then a piece of millipore filter was put thereon and the filter was impressed to collect samples of the epithelium cells of the conjuctive as well as the goblet cells. The collected cells were fixed with 70% ethanol and were stained by use of periodic acid-Schiff reaction (PAS) and hematoxylin, next the thus stained millipore filter was changed to transparent by use of xylene and was enclosed in the space of a preparative glass. The thus obtained sample in the preparative glass was photo-graphed, and the number of the goblet cells (mean value±S.E., n=4 eyes) per unit area (0.09 mm$^2$) was calculated. The results are shown in FIG. 2.

Figure 2:
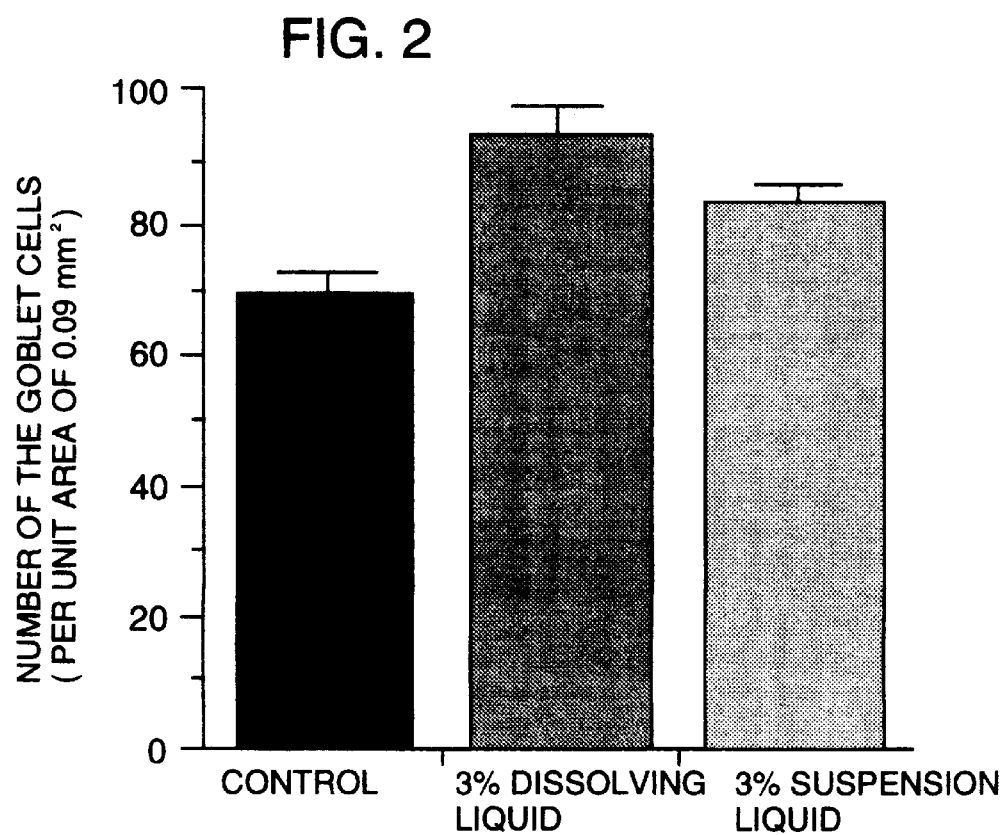
FIG. 2 shows a figure relating to the effect of carbostyril derivative of the present invention against the number of goblet cells in normal rabbits.

As can be seen from FIG. 2, the number of the goblet cells contained on the conjuctiva of the normal rabbits of the test group, to which 3% dissolving liquid and 3% suspension liquid (both of them containing the compound of the present invention, respectively) were administered by eye drop, was measured in the larger value as compared with those measured in the rabbits of the control group. Thus, the compound the present invention shows the effects for increasing the amount of mucoid substance and also increasing the amount of tear fluid as well.

(iii) Measurement of the amount of tear fluid (Measurement by Modified Method of Schirmer Test I)

To the normal rabbits of the test group being treated with the above-mentioned test liquids, 30 μl of Benoxil (a trade name for 0.4% of oxybuprocaine hydrochloride solution for eye drop use, manufactured by Santen Pharmaceutical Co., Ltd.) was administered by eye drop 5 minutes before the following test for measuring the amount of tears fluid. The rabbits were allowed to stand as they are for 4 minutes, and the tear fluid on the surface of the eyes were wiped off. Then, 1 minute after, a piece of Schirmer test paper was put in a space between the inside of the lower eyelid and the surface of the eye (the start for measuring the amount of tear fluid). The rabbits were allowed to stand as they were for 5 minutes, then the length (mm) (mean value±S.E., n=4 eyes) of tear fluid being permeated on the Schirmer test paper was measured. The results are shown in FIG. 3.

Figure 3:
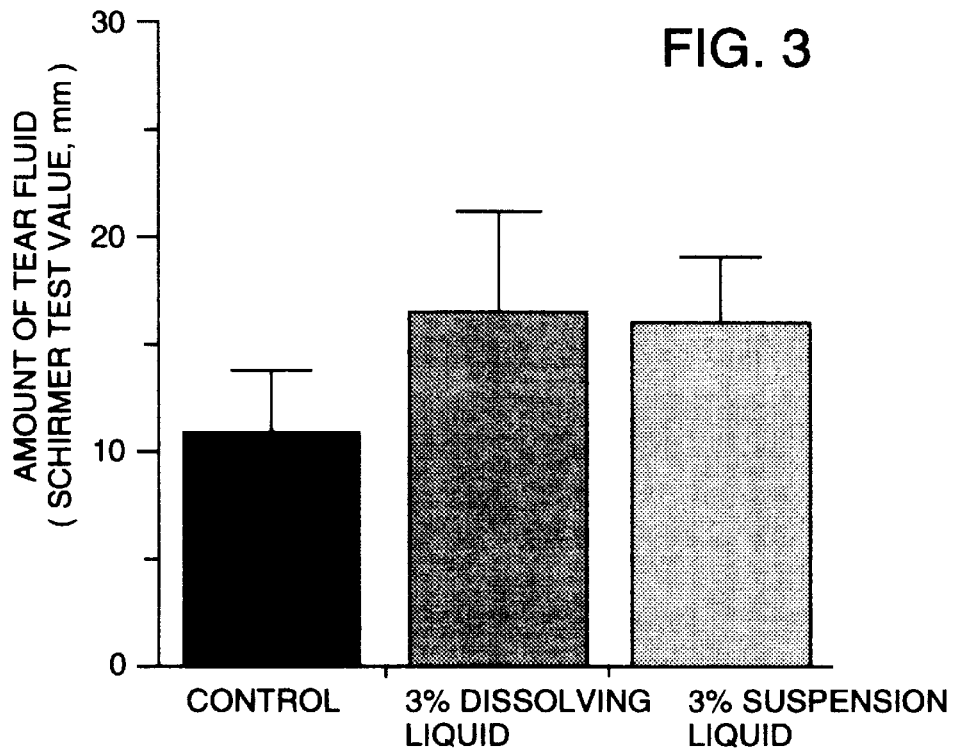
FIG. 3 shows a figure relating to the effect of carbostyril derivative of the present invention against the amount of tears secreted in normal rabbits.

As can be seen from FIG. 3, the amount of tear fluid of the normal rabbits of the test group, to which 3% dissolving liquid and 3% suspension liquid (both of them containing the compound of the present invention, respectively) were administered by eye drop, were measured in larger value as compared with those measured in the rabbits of the control group. Thus, the compound of the present invention shows the effects for increasing the amount of tear fluid as compared with those shown by the rabbit of the control group.

Pharmacological Test 2
(1) Experimental Method

The eyeballs were enucleated from New Zealand White female rabbit, and a sample piece of the sclerocornea was prepared. After peeled off the Descemet's membrane and the endotheliocyte from said sample piece under observation by use of a stereoscopic microscope, then the sample piece of the sclerocornea was washed 4 to 5 times with a phosphate buffered physiological saline so as to made the sample as in an aseptic condition (asepsis). Next, said aseptic sample piece of sclerocornea was soaked in a Dulbecco's modified Eagle's culture medium F12 (DME/F12) (1:1), and about 20 pieces of small square sample blocks having a side of 2–3 mm of the cornea were cut out from each one of all of the cornea samples by using a razor blade. Into a tissue culture dish having 60 mm in diameter, 7 to 8 pieces of these small sample blocks of the cornea were put in the dish and adhere the downside of the block to the bottom of the dish so as to keep the corneal epithelium upside, and were cultivated in a culture medium containing 10% FCS, 10 ng/ml of hEGF added-DME/F12 (1:1) under an atmosphere of 5% $CO_2$-95% air, at 37° C. After 2 days of cultivation, the small sample blocks of the corneal epithelium were took out from the culture medium and the medium was exchanged.

The cultivation was continued for 4–5 days (the culture medium was exchanged 1–3 times), then the culture medium was removed, the small sample blocks of the corneal epithelium were washed with a phosphate buffer solution, the cells were floated in a solution of 0.1% trypsin—0.02% EDTA, and was suspended in a culture medium of DME/F12 (1:1) containing 10% FCS, next the suspension was inoculated on a multiwell cultivating dish having 12 wells in an amount of 1×10$^4$ cells/well. After about 12 hours, the culture medium was exchanged to another medium of DME/F12 containing 1% FCS, and the compound of the present invention which was the same as used in Pharmacological Test 1 was dissolved in DMSO and added in the concentration of $10^{-4}$ to $10^{-6}$ M.

48 Hours after the addition of the compound of the present invention, the culture medium containing the compound of the present invention was exchanged. 96 Hours after the addition of the compound of the present invention, the cells were floated in a solution of 0.1% trypsin—0.02% EDTA, and the number of the cells was counted (mean value±S.E., n=6 eyes) by using a Coulter counter.

As to the reference test, sodium hyaluronate (1 mg/ml) was used in place of the compound of the present invention. As to the control test, DMSO without containing a compound of the present invention was used.

(2) Test Results

Figure 4:
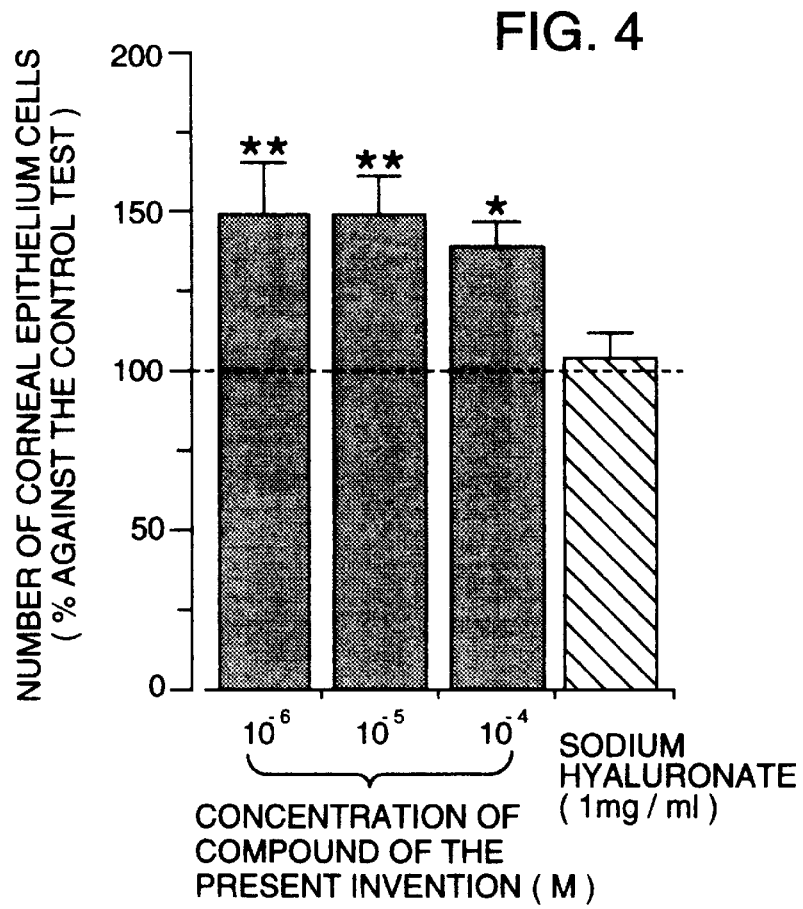
FIG. 4 shows a figure relating to the effect of carbostyril derivative of the present invention against the proliferation of the cornea epithelium cells in normal rabbits.

The results are shown in FIG. 4. As can be seen from FIG. 4, in case of treating the corneal epithelium with the compound of the present invention, excellent effect for increasing the proliferation of corneal epithelium was shown as compared with that shown in the reference test by using sodium hyaluronate which is recognized as a compound having the activity for increasing the proliferation of corneal epithelium. In the FIG. 4, the symbol "*" means p<0.05 vs control; and the symbol "*" means p<0.01 vs control.

Pharmacological Test 3

(Test of the dry eye model prepared by compulsive blowing)
(1) Test Liquid

As to the specific example of the effective ingredient of the agents for curing ophthalmological diseases of the present invention, 2-(4-chlorobenzoylamino)-3-(2-quinolon-4-yl)propionic acid (hereinafter referred to as the compound of the present invention) was used and prepared the following 1% eye drop liquid, and used it as test liquid.

| 1% Eye drop liquid | |
|---|---|
| The compound of the present invention | 0.50 g |
| Meglumine (N-Methylglucamine) | 1.32 g |
| Concentrated glycerin | 0.45 g |
| 10% Benzalkonium | 50 μl |
| Polysiological saline (an adequate amount was added to adjust the whole volume to:) | 50 ml |

-continued

| 1% Eye drop liquid | |
|---|---|
| pH (the pH value was adjusted to within the range of:) | 8.8 to 9.3 |
| Osmotic pressure (the osmotic pressure was adjusted to within the range of:) | 290 to 300 mOsm |

As to the control test, the above-mentioned dissolving agent of the eye drop without containing a compound of the present invention was used as the reference.

(2) Method for Preparing the Dry Eye Model (the mucoid capsulitis and injury of cornea epithelium)

A New Zealand White female rabbits were used for the test. The nictitating membrane of the rabbit was excised before the test.

To both eyes of the rabbit was administered, as anesthetics, by injecting in the muscle with 200 mg/body weight of Ketamin hydrochloride and dropping 4% of oxybuprocaine hydrochloride solution in the dosage of 2 drops/eye.

The distance between a dryer and the cornea was kept in 10 cm, and wind was blown from the dryer to the direction in front of the cornea for 10 minutes. The tear fluid was evaporated, and the surface of the cornea was dried, then the mucoid capsulitis and injury of cornea epithelium were induced thereby.

(3) Administration of the Test Compound

Two weeks before conducting the wind blowing from the dryer, the 1% eye drop liquid was administered. After preparation of the dry eye model by wind blowing from the dryer, the 1% eye drop liquid was administered for 2 weeks. Administrations of the 1% eye drop liquid were conducted 4 times/day at intervals of 2.5 hours before and after the administrations.

As to the control test, the dissolving agent of the eye drop without containing a compound of the present invention was used as the reference.

(4) Evaluation Method and the Results

Results of the test were evaluated regarding the following 2 items in connection with before administration with the 1% eye drop liquid; before conducting the wind blowing; 1, 4, 7, 10 and 14 days after the wind blowing.

(i) Score evaluation of the injured cornea by method of intravital staining with Rose Bengal colorant The cells of the cornea which were not covered with mucoid substance were stained by method of intravital staining with Rose Bengal colorant, and the mucoid capsulitis on the cornea of the rabbit of the test group were evaluated on the basis of the following score evaluations according to the stained degree of the cornea (mean value±S.E., n=10 eyes).

| Score evaluations (Perfect score: 3 points) | |
|---|---|
| Score 0: | The cornea was not stained at all. |
| Score 1: | Less than 1/3 of the area of the all cornea was stained uniformly, or less than 2/3 of the area of the cornea was stained spots. |
| Score 2: | 1/3–2/3 of the area of the all cornea was stained uniformly, or more than 2/3 of the area of the cornea was stained spots; or less than 1/3 of the area of the all cornea was stained uniformly, also stained spots was observed. |
| Score 3: | More than 2/3 of the area of the all cornea was stained uniformly, or 1/3–2/3 of the area of the all cornea was stained uniformly, also stained spots were observed. |

Figure 5:
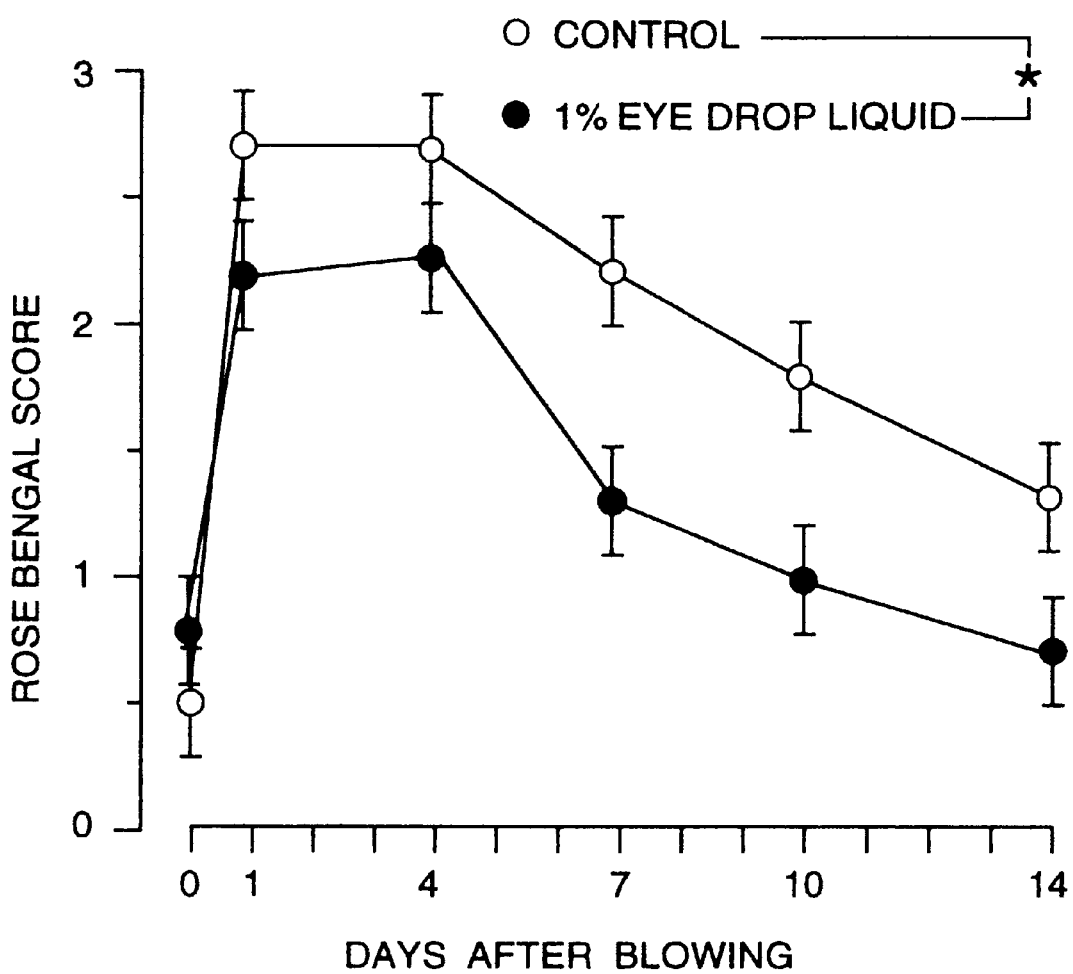
FIG. 5 shows a figure relating to the effect of carbostyril derivative of the present invention against the mucoid capsulitis in normal rabbits determined by a method of Rose Bengal score.

The results are shown in FIG. 5. As can be seen from FIG. 5, the cornea of the New Zealand White rabbits of the test group, to which the 1% eye drop liquid were administered, the score of intravital staining with Rose Bengal colorant are lower than those shown by the control group. Thus, the compound of the present invention significantly inhibits and cures the mucoid capsulitis caused by wind blowing method.

(ii) Score evaluation of the injured cornea by method of intravital staining with fluorescein-Na colorant Defective portion of the cells and abnormal portion of the intercellular space were stained by method of intravital staining with fluorescein-Na colorant, and the mucoid capsulitis on the cornea of the rabbit of the test group was evaluated on the basis of the scores according to the stained degree of the cornea similar to those employed in the above-mentioned intravital staining with Rose Bengal colorant (mean value±S.E., n=10 eyes).

As a result, comparing with the fluorescein score at 1 day after the wind blowing, the score of the control group was 2 or more, while the score of the New Zealand White rabbits of the test group, to which the 1% eye drop liquid were administered, was almost 1. Thus, the compound of the present invention significantly inhibits and cures mucoid capsulitis induced by wind blowing method.

Pharmacological Test 4

(Test of the dry eye model prepared by preventing of blinking)

(1) Test Liquid

1% Eye drop liquid (eye drop liquid containing 1% of the compound of the present invention), which is similar to the one employed in Pharmacological Test 3, was used as the test liquid.

As to the control test, dissolving agent of the eye drop without containing a compound of the present invention was used.

(2) Method for Preparing the Dry Eye Model

A New Zealand White female rabbits were used for the test. The nictitating membrane of the rabbit was excised before the test.

To both eyes of the rabbit was administered, as anesthetic, by injecting in the abdominal cavity with 2 g/body weight of uretan. The eyelids of the rabbit were compulsively kept open by use of an eye speculum, and were allowed to stand as they were at 25° C. for 2 hours. The tear fluid was evaporated, and the surface of the cornea was dried, an injured cornea epithelium as the dry eye model of was prepared.

(3) Administration of the Test Compound

Two weeks before the preventing of blinking, the 1% eye drop liquid was administered 4 times/day at intervals of 2.5 hours. The final administration with the eye drop liquid was conducted 5 minutes before the preventing of blinking.

As to the control test, the dissolving agent of the eye drop without containing a compound of the present invention was used as the reference.

(4) Evaluation Method and the Results

After finished the preventing of blinking, 50 μl of 1% methylene blue solution was administered by eye drop of the rabbit of the test group, and the eye was washed thoroughly with a physiological saline.

Then, the rabbit was killed by intravenous administration with an excessive amount of pentobarbital injection solution, and the cornea was enucleated. The methylene blue was extracted from the enucleated cornea by using a mixture of acetone : an aqueous solution saturated with sodium sulfate=7:3 by taking time for overnight. Optical density at 660 nm of the thus obtained extract was measured, and the methylene blue being stained to the injured portion of the cornea epithelium was calculated (mean value±S.E., n=8 eyes).

Figure 6:
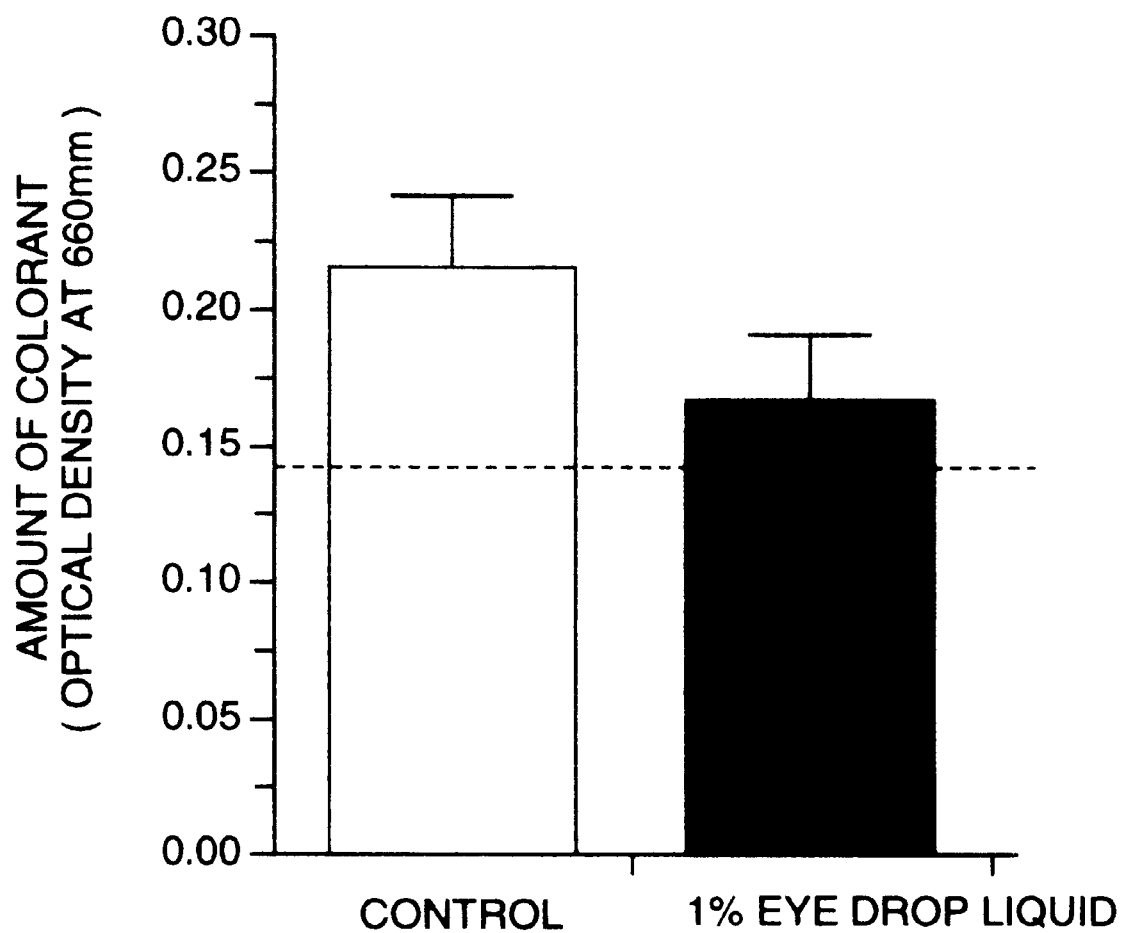
FIG. 6 shows a figure relating to the effect of carbostyril derivative of the present invention against injury of the corneal epithelium in normal rabbits caused by preventing of blinking.

Results are shown in FIG. 6. As can be seen from the FIG. 6, the compound of the present invention inhibits the injury of the corneal epithelium induced by preventing of blinking.

Pharmacological Test 5

(Test of the dry eye model prepared by removal of the mucoid layer from the conjuctiva)

(1) Test Liquid

1% Eye drop liquid (eye drop liquid containing 1% of the compound of the present invention), which is similar to the one employed in Pharmacological Test 3, was used as the test liquid.

As to the control test, dissolving agent of the eye drop without containing a compound of the present invention was used.

(2) Method for Preparing the Dry eye Model

The dry eye model was prepared by dissolving and removing the mucoid layer from the conjuctiva of a New Zealand White female rabbit by instillation with an N-acetylcysteine solution of 10% in concentration, by means of eye drop 6 times at intervals of 2 hours for 1 day.

(3) Administration of the Test Compound

1% Eye drop liquid was administered 4 times/day at intervals of 2.5 hours and were continued for 2 weeks.

As to the control test, the dissolving agent of eye drop liquid without containing a compound of the present invention was used as the reference.

(4) Evaluation Method and the Results

2 Weeks after the beginning of administration of the 1% eye drop liquid, the rabbit was killed by intravenous administration of an excessive amount of pentobarbital injection solution, then the cornea was enucleated. The amount of the mucoid substance covering on the conjuctiva was measured by a procedure similar to that employed in Alcian Blue binding method in Pharmacological Test 1, (2) (i) (mean value±S.E., n=6 eyes).

Figure 7:
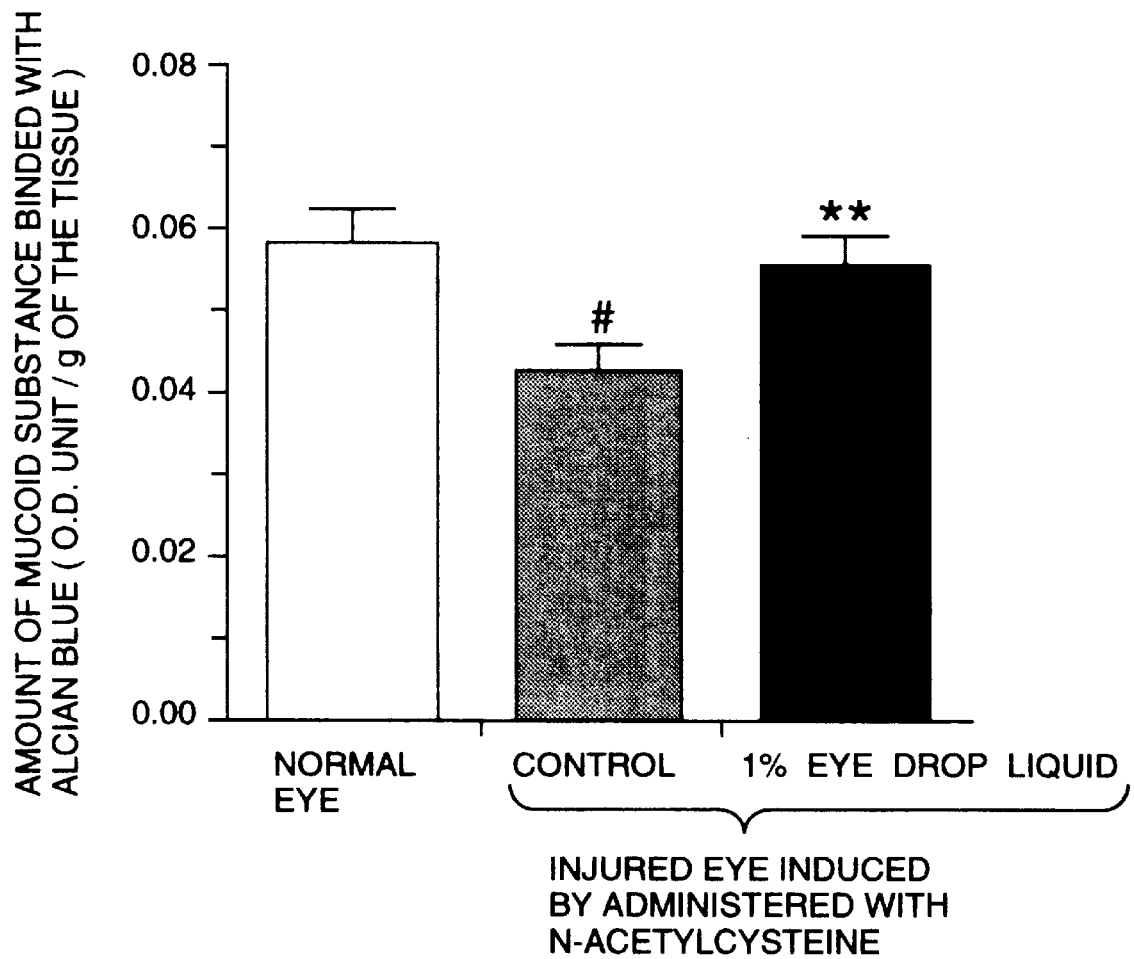
FIG. 7 shows a figure relating to the effect of carbostyril derivative of the present invention against the increased amount of mucoid substance covering the conjuctiva in normal rabbits of which the mucoid layer was removed and determined by an Alcian blue blinding method.

The results are shown in FIG. 7. As can be seen from FIG. 7, the amount of the colorant binded onto the mucoid substance covering on the conjuctiva in the New Zealand White rabbits of the test group, to which the 1% eye drop liquid were administered, the amount of the mucoid substance covering on the conjuctiva are higher than those shown by control group. Thus, the compound of the present invention increases the amount of the mucoid substance covering on the conjuctiva up to almost the same level as on the surface of the eyes in normal state.

In FIG. 7, the symbol "#" means p<0.05 vs. the eyes in normal state (t-test); and the symbol "**" means p<0.01 vs. the eyes of control group (t-test).

We claim:

1. A method for treating xerophthalmia syndrome by administering to a patient in need thereof an agent which contains, as the active ingredient, a carbostyril compound or a salt thereof represented by the general formula (I),

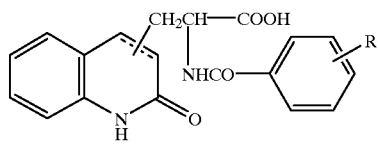

(I)

(wherein R is a halogen atom, the substituted position of the side-chain of the formula,

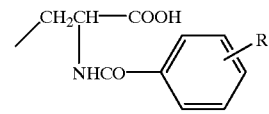

is at the 3- or 4-position in the carbostyril skeleton, and the carbon-carbon bond between the 3- and 4-positions in the carbostyril skeleton is a single bond or a double bond).

2. A method for accelerating proliferation of goblet cells in the eye, for treating xerophthalmia syndrome, by administering to a patient in need thereof an agent which contains, as the active ingredient, a carbostyril compound or a salt thereof represented by the general formula (I),

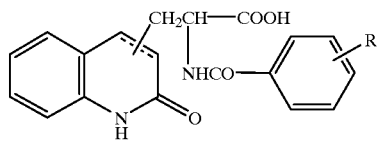

(I)

(wherein R is a halogen atom, the substituted position of the side-chain of the formula,

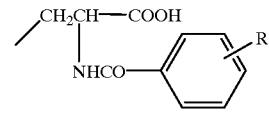

is at the 3- or 4-position in the carbostyril skeleton, and the carbon-carbon bond between the 3- and 4-positions in the carbostyril skeleton is a single bond or a double bond).

3. A method for increasing the amount of mucoid substance secreted in the eye, for treating xerophthalmia syndrome, by administering to a patient in need thereof an agent which contains, as the active ingredient, a carbostyril compound or a salt thereof represented by the general formula (I),

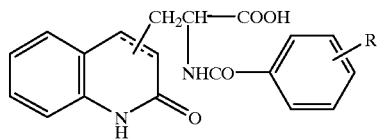

(I)

(wherein R is a halogen atom, the substituted position of the side-chain of the formula,

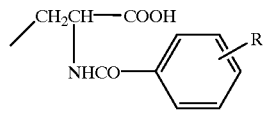

is at the 3- or 4-position in the carbostyril skeleton, and the carbon-carbon bond between the 3- and 4-positions in the carbostyril skeleton is a single bond or a double bond).

4. A method for increasing the amount of tear fluid secreted in the eye, for treating xerophthalmia syndrome, by administering to a patient in need thereof an agent which contains, as the active ingredient, a carbostyril compound or a salt thereof represented by the general formula (I),

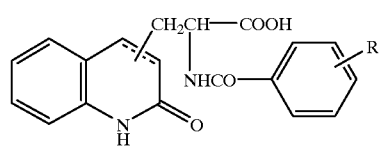 (I)

(wherein R is a halogen atom, the substituted position of the side-chain of the formula,

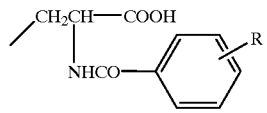

is at the 3- or 4-position in the carbostyril skeleton, and the carbon-carbon bond between the 3- and 4-positions in the carbostyril skeleton is a single bond or a double bond).

5. A method for accelerating proliferation of corneal epithelium cells in the eye, for treating xerophthalmia syndrome, by administering to a patient in need thereof an agent which contains, as the active ingredient, a carbostyril compound or a salt thereof represented by the general formula (I),

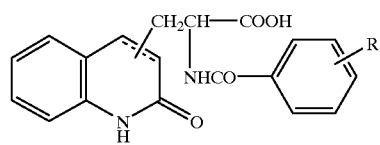 (I)

(wherein R is a halogen atom, the substituted position of the side-chain of the formula,

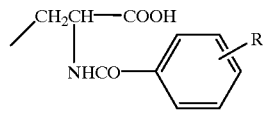

is at the 3- or 4-position in the carbostyril skeleton, and the carbon-carbon bond between the 3- and 4-positions in the carbostyril skeleton is a single bond or a double bond).

6. The method for treating xerophthalmia syndrome according to claim 1, wherein the active ingredient is 2-(4-chlorobenzoylamino)-3-(2-quinolon-4-yl)propionic acid or a salt thereof.

7. The method for accelerating proliferation of goblet cells in the eye according to claim 2, wherein the active ingredient is 2-(4-chlorobenzoylamino)-3-(2-quinolon-4-yl)propionic acid or a salt thereof.

8. The method for increasing the amount of mucoid substance secreted in the eye according to claim 3, wherein the active ingredient is 2-(4-chlorobenzoylamino)-3-(2-quinolon-4-yl)propionic acid or a salt thereof.

9. The method for increasing the amount of tear fluid secreted in the eye according to claim 4, wherein the active ingredient is 2-(4-chlorobenzoylamino)-3-(2-quinolon-4-yl) propionic acid or a salt thereof.

10. The method for accelerating proliferation of corneal epithelium cells in the eye according to claim 5, wherein the active ingredient is 2-(4-chlorobenzoylamino)-3-(2-quinolon-4-yl)propionic acid or a salt thereof.

11. The method according to any one of claims 6–10 wherein the agent is in the form of a pharmaceutical preparation suitable for opthalmological application.

12. The method according to claim 11, wherein the pharmaceutical preparation suitable for opthalmological application is an eye drop preparation or oculentum.

13. The method according to claim 11, wherein the amount of the active ingredient contained in the agent is from 0.005 to 5% by weight.

14. The method according to claim 12, wherein the amount of the active ingredient contained in the agent is from 0.005 to 5% by weight.

15. The method according to claim 13, wherein the amount of the active ingredient contained in the agent is from 0.01 to 3% by weight.

16. The method according to claim 14, wherein the amount of the active ingredient contained in the agent is from 0.01 to 3% by weight.

* * * * *